US012697442B2

(12) United States Patent
Martini

(10) Patent No.: US 12,697,442 B2
(45) Date of Patent: Aug. 4, 2026

(54) INJECTION NEEDLE HAVING VARYING CALIBER

(71) Applicant: David Vincent Martini, Douglas, GA (US)

(72) Inventor: David Vincent Martini, Douglas, GA (US)

( * ) Notice: Subject to any disclaimer, the term of this patent is extended or adjusted under 35 U.S.C. 154(b) by 576 days.

(21) Appl. No.: 18/141,508

(22) Filed: May 1, 2023

(65) Prior Publication Data

US 2023/0285687 A1     Sep. 14, 2023

Related U.S. Application Data

(63) Continuation-in-part of application No. 16/558,024, filed on Aug. 30, 2019, now abandoned.

(51) Int. Cl.
*A61M 5/32*          (2006.01)

(52) U.S. Cl.
CPC ....... *A61M 5/3298* (2013.01); *A61M 2207/10* (2013.01)

(58) Field of Classification Search
CPC .................. A61M 25/0068; A61M 2005/3284
See application file for complete search history.

(56) References Cited

U.S. PATENT DOCUMENTS

| | | | | |
|---|---|---|---|---|
| 10,702,672 | B2 * | 7/2020 | Lampropoulos .. | A61M 25/0026 |
| 2009/0234288 | A1 * | 9/2009 | Fischer ................... | A61M 5/34 |
| | | | | 604/117 |
| 2014/0276622 | A1 * | 9/2014 | Racz .................. | A61B 17/3401 |
| | | | | 604/512 |
| 2016/0243316 | A1 * | 8/2016 | Martini .............. | A61B 17/3478 |
| 2016/0361088 | A1 * | 12/2016 | Maguire ............ | A61B 17/3415 |

\* cited by examiner

*Primary Examiner* — Dung T Ulsh
(74) *Attorney, Agent, or Firm* — Dale J. Ream

(57) ABSTRACT

An injection needle includes a first needle portion defining a first outer diameter, a second needle portion defining a second outer diameter that is smaller than the first outer diameter, the second needle portion having a tip configured to penetrate a soft tissue. Importantly, the first end of the second needle portion is positioned substantially inside and coupled to an inner surface of the first needle portion adjacent an angled section that is positioned adjacent a distal end of the first needle portion. In addition, the first and second needle portions may be crimped or pinched together into a unitary construction that still allows a pharmaceutical to pass therethrough.

17 Claims, 4 Drawing Sheets

108

100

102

102a

104

102b

106b

110

106

108

100

102a

102

104

106b

102b

110

202

200

202a

202b

204

214

206a

210

INJECTION NEEDLE HAVING VARYING CALIBER

REFERENCE TO RELATED APPLICATIONS

This application is a continuation-in-part of U.S. patent Ser. No. 16/558,024, filed Aug. 30, 2019, entitled Injection Needle Having Varying Caliber, the disclosure of which is incorporated herein by reference.

BACKGROUND OF THE INVENTION

This invention relates generally to injection needles, and, more particularly, to an injection needle having a 1) first portion having a tubular configuration defining a first diameter and that is constructed for strength and stability and a 2) second portion having a tubular configuration defining a second diameter that is smaller than the first diameter that is positioned inside and coupled to the first portion. In addition, the first portion may include a bend (i.e., a bent portion) at or proximate to a connection of the second portion to the first portion.

An injection needle is typically used by a health care professional (e.g., a surgeon or nurse) to administer pharmaceutical drugs to a patient. Often, circumstances require the injection needle to be administered where physical spacing is limited. Large diameter (smaller needle gauge number) injection needles allow for precision administration of the pharmaceuticals due to their low flexibility; however, the larger the injection needle, generally the more pain and tissue damage the patient will experience. By contrast, small diameter (large needle gauge number) injection needles offer high flexibility allowing for improved maneuverability and lower tissue damage/pain. Yet, because small diameter injection needles are flexible, it is more difficult to administer the pharmaceuticals to the precise location at which the health care professional intends. Additionally, during the injection of medication, excess medication will spill out from the tissues and have an adverse effect on the patient.

In an example procedure such as delivering a medication to the sinuses of a patient, a small diameter and flexible injection needle may be needed for the tissue of the sinuses that will have the medication injected. However, because the sinuses may need to be accessed through the patient's nostrils, the flexibility of such a needle presents problems as it may lack a stiffness that may be needed to guide the needle through the nostrils to the target of the sinuses. In addition, the small diameter injection needle is likely to be susceptible to breakage or damage before or during the procedure. Thus, a small diameter needle with a more rigid body to guide the needle may be desired. Other procedures for which the present injection needle may be useful include septal deviations, septal spur, turbinate hypertrophy and other anatomic conditions blocking needle injection pathway.

Therefore, it would be desirable to have an injection needle having 1) a first portion having a tubular configuration constructed of a strong and rigid material and defining a first diameter and 2) a second portion having a tubular configuration constructed of a flexible material and defining a second diameter that is smaller than the first diameter such that the injection needle is more likely to reach a desired surgical location without breakage while still having the efficacy of high maneuverability and less damage to a patient's tissues. Further, it would be desirable to have an injection needle in which the first portion includes a bent portion such that the injection needle per se has a curved shaft for optimal access to a patient's sinus cavity.

SUMMARY OF THE INVENTION

The present invention includes an injection needle including a first needle portion having a first outer diameter and a second needle portion having a second outer diameter smaller than the first outer diameter and a tip configured to penetrate tissue of a patient to deliver medication.

Therefore, a general object of this invention is to provide an injection needle having a first portion defining a first diameter tubular configuration and a second needle portion that is mounted partially inside the first portion and which defines a second diameter that is smaller than the first diameter and which includes a needle tip that is flexible and well received into a patient's tissue.

Another object of this invention is to provide an injection needle, as aforesaid, in which a first end of the second needle portion is coupled to a distal end of the first needle portion using crimping substantially at the location of the angle section.

Other objects and advantages of the present invention will become apparent from the following description taken in connection with the accompanying drawings, wherein is set forth by way of illustration and example, embodiments of this invention.

The foregoing and/or other aspects and advantages of the present general inventive concept may be achieved by an injection needle including a first needle portion having a first outer diameter, and a second needle portion having a second outer diameter, the second outer diameter being smaller than the first outer diameter, wherein the second needle portion has a tip configured to penetrate a soft tissue. Importantly, the proximal end of the second needle portion is positioned substantially inside and coupled to an inner surface of the first needle portion. In addition, the first and second needle portions may be crimped or bent together into a unitary construction that still allows a pharmaceutical to pass therethrough. The foregoing and/or other aspects and advantages of the present general inventive concept may be achieved by an injection needle.

The foregoing and/or other aspects and advantages of the present general inventive concept may also be achieved by an injection needle including a hub portion configured to mate with a corresponding hub portion of a medication delivery device, and a needle attached at a proximal end to the hub and configured to have a first outer diameter extending in a longitudinal direction from the hub, the first outer diameter having a bend portion proximate a distal end of the needle, the bend portion having a predetermined angle matching a corresponding tissue path through which the needle will pass to enter a targeted region of the patient, the needle including a distal end configured to have a second outer diameter smaller than the first outer diameter, the second diameter terminating to a needle tip for delivery of medication into the targeted region, the first diameter being specifically sized to push away bodily tissue in the tissue path a distance sufficient to provide an opening for the second diameter to enter the targeted at the predetermined angle to deliver medication to the targeted region.

DESCRIPTION OF THE PREFERRED EMBODIMENT

Figures 1A, 1B, 1C:
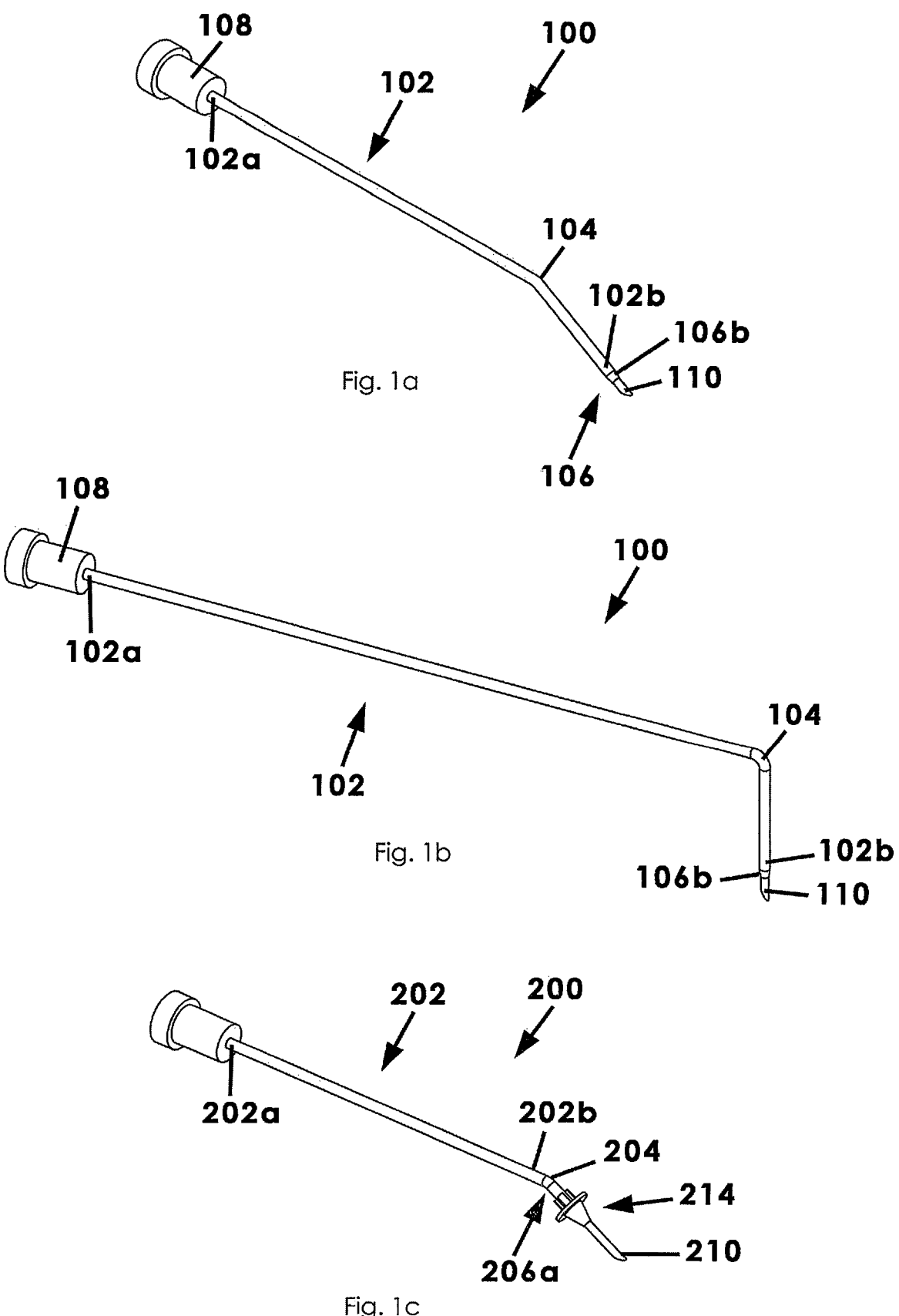
FIG. 1a is a front view of an injection needle according to a preferred embodiment of the present invention.
FIG. 1*b* is a front view of an injection needle according to another example embodiment of the present invention.
FIG. 1*c* is a front view of an injection needle according to still another example embodiment of the present invention.
Figure 2A:
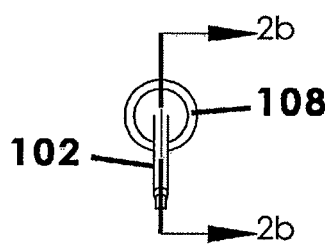
FIG. 2*a* is an end view of the injection needle as in FIG. 1*a*.
Figure 2B:
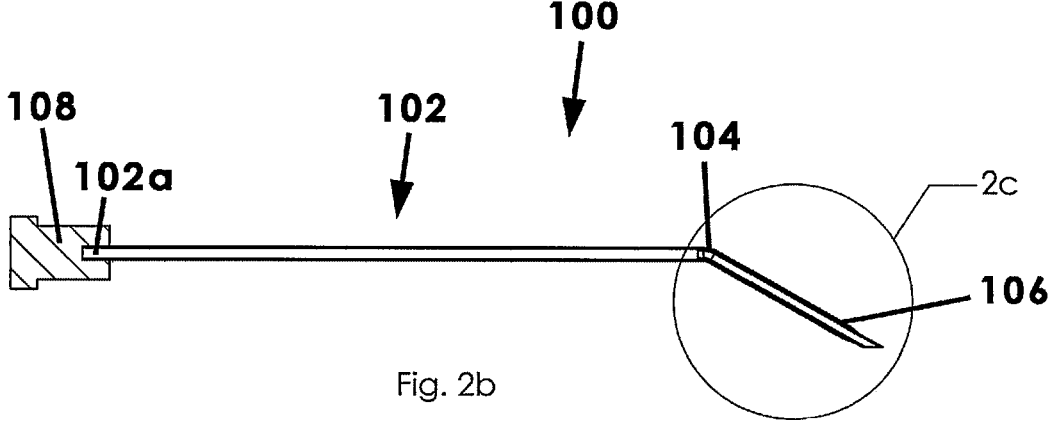
FIG. 2*b* is a sectional view taken along line 2*b*-2*b* of FIG. 2*a*.
Figure 2C:
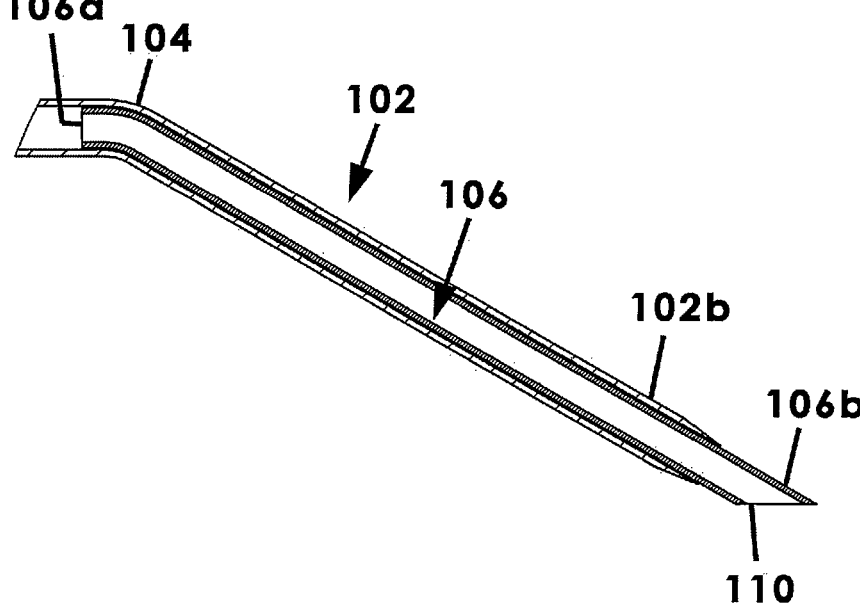
FIG. 2*c* is an isolated view on an enlarged scale taken from FIG. 2*b*.

An injection needle according to a preferred embodiment of the present invention will now be described with reference to FIGS. 1 to 4*c* of the accompanying drawings.

The following detailed description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. The described progression of processing operations described are merely examples, however, and the sequence of operations is not limited to that set forth herein and may be changed as is known in the art, with the exception of operations necessarily occurring in a certain order. Also, description of well-known functions and constructions may be omitted for increased clarity and conciseness. Various example embodiments of the present general inventive concept, as described herein, provide an injection needle of varying caliber such that a first portion of the injection needle is more rigid than a second portion of the injection needle having a tip that is used to inject medication into a patient. An example embodiment may provide an injection needle including a first needle portion having a first outer diameter, and a second needle portion having a second outer diameter smaller than the first outer diameter and a tip configured to penetrate tissue of a patient to deliver medication. Thus, a user administering the medication is able to take advantage of the higher rigidity of the larger diameter portion to guide the smaller diameter portion to the desired injection point to deliver the medication. To provide even further advantage to the user administering the medication in situations that present difficult to reach places such as sinuses that are accessed through a patient's nostrils, an example embodiment of the present general inventive concept may provide an injection needle including a guide portion configured to have a first outer diameter, and a delivery portion, configured with a tip to penetrate tissue and deliver a medication, and to have a second outer diameter smaller than the first outer diameter, extending from a distal end of the guide portion, wherein the guide portion is configured to have a bend proximate the distal end such that the delivery portion extends at a predetermined angle from a line or axis of the guide portion opposite the bend.

Various example embodiments herein may describe a first portion of an injection needle that has a first outer diameter greater than a second outer diameter of a second portion of the injection needle. The first portion having the larger outer diameter may be interchangeably referred to as a "guide" portion, as the increased rigidity of the larger diameter portion may be used to more effectively guide the injection needle through various cavities, openings, etc., of the body of the patient than the conventional needle having only one continuous outer diameter, which may be too flexible for such guidance due to the required injection tip size. Similarly, the second portion having the smaller diameter and injection tip may be interchangeably referred to as a "delivery" portion, as the increased flexibility of the smaller diameter portion may be more effective in injecting the tip into the actual desired tissue.

For example, the injection needle can be specifically configured to have a first outer diameter extending in a longitudinal direction from a hub portion, the first outer diameter having a bend portion (also referred to as an angled section) proximate a distal end of the needle to provide a predetermined angle matching a corresponding tissue path of the patient through which the needle will pass. The first diameter is sized to push bodily tissue in the tissue path away from the tissue path a distance sufficient to create an opening for the second diameter to enter the targeted region at the predetermined angle to deliver medication to the targeted region without causing the second diameter to bend.

As described herein, the present general inventive concept relates to an injection needle of varying caliber (i.e., outer diameter/gauge). Specifically, the present general inventive concept relates to an injection needle that includes a smaller diameter needle proximate a needle tip, and a larger diameter needle as the main shaft. Varying diameter injection needles have a variety of advantages, such as increased precision and a decrease in tissue damage, which correspond with low pain upon injection.

FIG. 1 illustrates an injection needle 100 according to an example embodiment of the present inventive concept. In this example embodiment, the injection needle 100 includes a hub 108, a first needle portion 102, a second needle portion 106, an angled section 104 positioned intermediate the first and second needle portions. More particularly, the first needle portion 102 includes a proximal end 102*a* and a distal end 102*b* opposite the proximal end 102*a*, the first needle portion 102 having a generally linear configuration. Similarly, the second needle portion 106 includes a first end 106*a* and a second end 106*b* opposite the first end 106*a*, the second needle portion 106 having a generally linear configuration. Described now in greater detail, the hub 108 may be a hub configured to mate with a corresponding similar hub of, for example, a syringe or other medication delivery device. In some example embodiments, the hub 108 may be configured to mate with a syringe. In other example embodiments, the hub 108 may be a Luer-Lok™ hub configured to mate with other similar Luer-Lok™ devices. In the illustrated example embodiment, the hub 108 is secured to the proximal end 102*a* of first needle portion 102. Again, the angled section 104 (also referred to as a bend portion 104) is positioned intermediate the distal end of the first needle portion 102 and a downstream portion of the second needle portion 106 and will be described in more detail later.

In the example embodiment of the injection needle 100, the first needle portion 102 has a tubular configuration having a linear and elongate configuration and defining a predetermined first outer diameter. Similarly, the second needle portion 106 has a tubular configuration having a linear configuration and defining a predetermined second outer diameter. In an embodiment, the first outer diameter is larger than the second outer diameter. It is understood that the first outer diameter and second outer diameter may be referred to merely as a first diameter and second diameter. Preferably, the first needle portion 102 is constructed of a generally rigid material such as metal or hard plastic so that the first needle portion 102 is robust and suitable for positioning the injection needle 100 at a desired location, such as being passed through a patient's nasal passages and into proximity with the patient's sinus cavities and sinus tissues that will be later impacted by a needle tip 110 which may be coupled to the second needle portion 106 as described later.

By contrast, the second needle portion 106, having a smaller diameter than that of the first needle portion 102, and may be constructed of materials allowing the second needle portion 106 to be more flexible. It is understood that the enhanced flexibility and smaller size enables the second needle portion 106 and needle tip 110 to be inserted into tissue with more accuracy and being able to move therein to one or more desired locations during surgery.

Figure 3A:
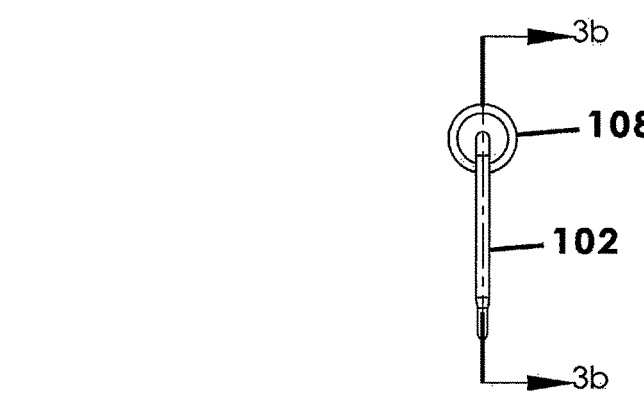
FIG. 3*a* is an end view of the injection needle as in FIG. 1*b*.
Figure 3B:
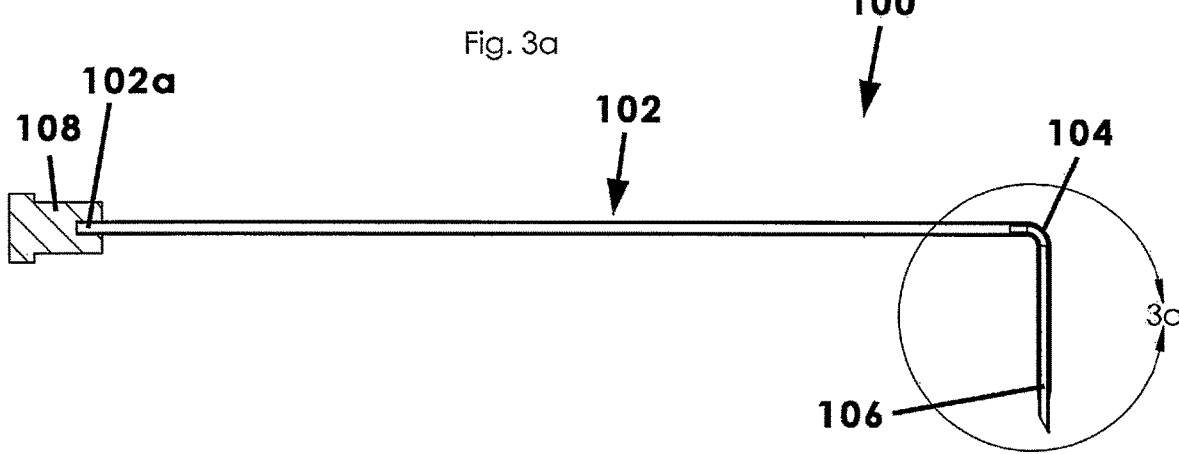
FIG. 3*b* is a sectional view taken along line 3*b*-3*b* of FIG. 3*a*.
Figure 3C:
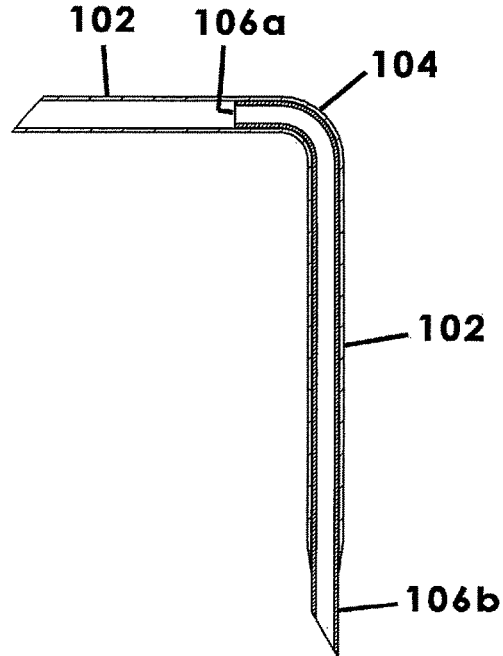
FIG. 3*c* is an isolated view on an enlarged scale taken from FIG. 3*b*.

At this point, the critical aspect of how and where the second needle portion 106 is coupled to the first needle portion 102 may be described in detail. In the broadest sense, the first end 106a of the second needle portion 106 is positioned inside the tubular channel defined by the first needle portion 102 at a point intermediate the proximal and distal ends 102a, 102b thereof, the first end 106a of the second needle portion 106 being coupled to an interior surface of the first needle portion 102. And, more particularly to the description above, the bend portion 104 is positioned at the distal end 102b of the first needle portion 102. Therefore, in a more narrow or more particular embodiment, the first end 106a of the second needle portion 106 is positioned immediately upstream of the bend portion 104 defined by the first needle portion 102 (FIG. 3b). It is understood, of course that the ends of the first needle portion 102 and the second needle portion 106 are open so that medicine, such as anesthetic fluid, may pass through the tubular channels defined by each, respectively.

As will be described in greater detail later, respective walls of the first and second needle portions may be crimped together using a respective manufacturing process that may result in greater strength and rigidity.

As described briefly above, the second needle portion 106 may include a needle tip 110 coupled to the second end 106b of the second needle portion 106. The tip 110 has a smaller diameter than the first needle portion 102. In some example embodiments, the tip 110 is an integral part of the injection needle 100. In other example embodiments, the tip 110 can be a modular portion of the injection needle 100. In various example embodiments, the tip 110 can be about 4 millimeters to 10 millimeters in length and have about a 27-gauge needle. Other various example embodiments may include different lengths and gauges. In an embodiment, the needle tip 110 is or includes a hypodermic needle.

With further reference to FIG. 1, the injection needle 100 includes a hub 108, the first needle portion 102 (which may also be referred to as a main shaft and also referred to with reference character 102), and a second needle portion 106. The illustrated example embodiment is configured for use as a nose/sinus local anesthesia injection needle.

In the example embodiment illustrated in FIG. 1, the main shaft 102 has an outer diameter to allow sufficient precision by the user when positioned at the site of injection on a patient. In some example embodiments, the first needle portion 102 (also referred to as the main shaft 102) may be a 16-gauge needle and may have a length of about 80 millimeters. At the opposite end of the main shaft 102 from the hub 108 is the needle end or tip 110. As illustrated in this example embodiment, not only is the second needle portion 106 of a significantly smaller outer diameter than that of the first needle portion 102, the needle tip 110 is also angled away from most of the first needle portion 102. This angle is facilitated by the bend portion 104 provided proximate the distal end 102b of the first needle portion 102. It is noted that in this example embodiment the outer diameter of the main shaft 102 is maintained on both sides of the bend portion 104.

In an embodiment, an injection needle 100 is configured to be attached to a syringe or other like medical device; however, it is contemplated as part of the present general inventive concept that a syringe or like medical device can be an integral part of the injection needle 100. In some example embodiments, the injection needle 100 may be configured to be reusable. In other example embodiments, the injection needle 100 may be configured to be disposable after a single use.

As discussed previously, in some example embodiments, the first needle portion 102 may include an angled section 104 (also referred to as a bend portion 108). Depending on certain applications, the angle section 104 may define an angle that may range from about 0 degrees to about 90 degrees. In the example embodiment illustrated in FIG. 1, which includes sinus operations as a possible use, the illustrated angle being about 37 degrees.

As discussed in relation to various example embodiments described herein, the bend or bend portion of the injection needle may be configured such that the relatively sturdier larger diameter first needle portion is able to push away bodily tissue in a tissue path so as to provide access for the smaller diameter second needle portion 106 and needle tip 110 to enter a targeted body region at a predetermined angle to deliver medication to the targeted region. The present general inventive concept may include several such angles, such as the examples discussed herein, but is not limited to any such configuration. For example, in a medical procedure in which a medical practitioner or user wishes to deliver medication through the injection needle to, for example, the frontal sinus of a patient, the location of the sinus with respect to anatomical structures such as the middle turbinate, ethmoid bulla, middle uncinate, etc., results in a situation in which the medical practitioner needs to both reach around anatomic corners and displace anatomic structures. For example, the user may need to displace such structures as the middle turbinate and middle uncinate, and angle around (or "wrap" around), for example, the middle turbinate and ethmoid bulla, for accurate placement of the needle tip in or at the sinus. An injection needle according to various example embodiments of the present general inventive concept allows the user to both displace and reach around such structures, as the case may be. As another example procedure, a medical practitioner may need to access the maxillary sinus. Similar to the procedure employed to access the frontal sinus, to accurately access the maxillary sinus the configuration of the injection needle according to the present general inventive concept allows the user to displace the middle turbinate and angle around the middle uncinate, and the angle of the bend of the injection needle allows access to the maxillary sinus, which is laterally located to the nasal cavity. As another example, to more conveniently and accurately access the sphenoid recess (or sinus), which is located posteriorly in the nasal cavity, the length, rigidity, and angulation of the injection needle of the present general inventive concept allows the user to reach such a deep cavity by angling around the middle uncinated while displacing the middle turbinate and superior turbinate to expose the sphenoid sinus. As yet another example, to conveniently and accurately access the ethmoid sinus, the length, rigidity, and angulation of the injection needle of the present general inventive concept allows the user to reach and access the ethmoid sinuses while pushing the middle turbinate out of the way of the injection needle. As previously described herein, an angle of 37 degrees of the needle tip relative to the guide portion on the opposite end of the bend from the needle tip may be used to access one or more of these described sinuses. In various example embodiments, the injection needle may be configured with bends of different angles from about 370 to 120°.

Also, as described herein, the injection needle of the present general inventive concept is not limited to applications related to nasal passages and sinuses, but may be used in a host of procedures in which such a rigid length of a guide portion aids in the placement of an angled delivery portion having a needle tip. For example, in a procedure in which a medical practitioner may need to deliver medication to a back area of the tongue of a patient, the configuration of the injection needle according to an example embodiment of the present general inventive concept provides a sufficient length to span the length of the tongue and deposit the medication, such as anesthesia at a tongue base and middle and/or posterior aspects of the tongue, uvula, pharynx area, etc. In an example embodiment, a 90-degree angle at the bend of the injection needle may be desired to perform such a procedure (FIGS. 1b and 3b). Depending on the application, the bend of the injection needle may be in a range from about 37° to about 120°.

Figure 4A:
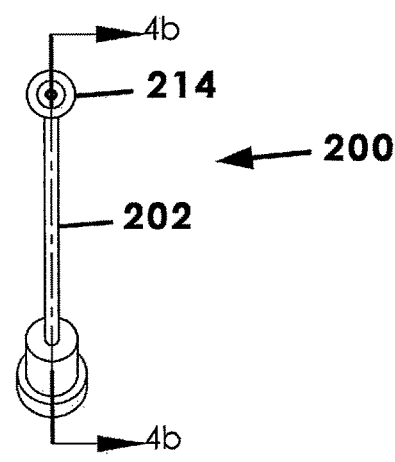
FIG. 4*a* is a side view of the injection needle as in FIG. 1*c*.
Figure 4B:
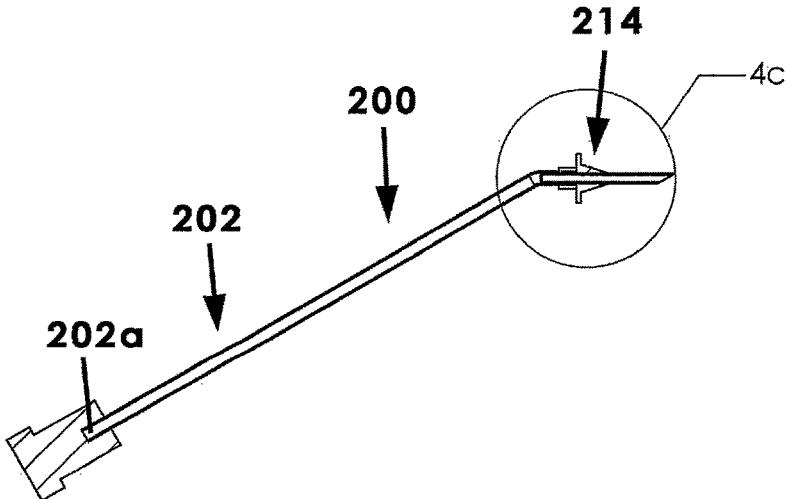
FIG. 4*b* is a sectional view taken along line 4*b*-4*b* of FIG. 4*a*.
Figure 4C:
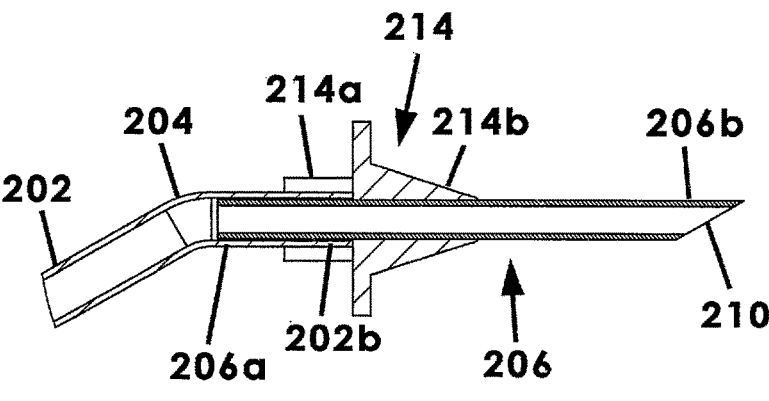
FIG. 4*c* is an isolated view on an enlarged scale taken from FIG. 4*b*.

Another example embodiment according to the present invention will be referred to as injection needle 200 and is shown in FIG. 1c and, more particularly, in FIGS. 4b and 4c. Injection needle 200 includes a construction substantially similar to the injection needle 100 described previously except as specifically described below. Accordingly, the injection needle 200 may include a first needle portion 202 having proximal and distal ends 202a, 202b, a second needle portion 206 having first and second ends 202a, 202b, with an angled section 204, each being formed or connected substantially as described in the first example embodiment. Specifically, a safety stop 214 may be provided proximate to (and, preferably, downstream of) the bend portion 204. In other words, the safety stop 214 may be positioned at or adjacent to the distal end 202b of the first needle portion 202. In fact, the safety stop 214 may include a mounting section 214a that is coupled to the distal end 202b of the first needle portion 102 and a body section 214b coupled to the second needle portion 106 that extends through and away from the distal end 202b of the first needle portion 202 (FIG. 4c). It is understood that the safety stop 214 may be coupled to respective needle portions using glue.

In use, the safety stop 214 may be a circular flange, lip, ridge, etc., on the injection needle 200 that prevents the user of the injection needle 200 from inserting the needle tip too far into the tissue of a patient. The safety stop 214 may be sized to physically stop the penetration of the injection needle 200 past the safety stop 214. The safety stop 214 may be configured to allow the user of the injection needle 200 to insert the injection needle 200 at the proper depth in the patient's tissue even when the user cannot physically see the injection site. In the illustrated example nose/sinus local anesthesia injection needle embodiment, the safety stop 214 has an outer diameter of about 1.5 millimeters. In various example embodiments, the safety stop 214 may be adhered to the main shaft by a variety of methods and/or adhesives, and may be formed of a different material than the injection needle 200. Various other example embodiments may omit the safety stop 214 entirely.

Although the example embodiments in FIGS. 1a-4a illustrate an injection needle having one configuration, a host of other configurations are possible in other various example embodiments of the present general inventive concept. For example, a large variety of lengths and diameters of the diameter injection needles can be created depending on the medical application. Further, the angles the needle ends make with the main shafts can be modified for many different specific applications.

While the various example embodiments illustrated and/or discussed herein have been discussed in terms of human patients, it is understood that various example embodiments of the present general inventive concept may be configured for use in veterinary procedures without departing from the scope and spirit of the present general inventive concept.

The example embodiments of injection needles described above may be constructed and formed according to the methods and processes discussed below. The initial steps of constructing or forming an injection needle according to the present invention have been substantially described previously. Namely, a first needle portion 102 is constructed using a rigid material such as hard plastic or even metal and includes opposed proximal and distal ends and has a tubular configuration that defines a first outer diameter. Similarly, a second needle portion 106 may be constructed using a semi-flexible material into a tubular configuration having first and second ends so as to define a second outer diameter that is smaller than the first outer diameter. A needle tip 110 may be mounted to the second end 106b of the second needle portion 106. The first end 106a of the second needle portion 106 may be slidably positioned at a position intermediate the proximal and distal ends of the first needle portion 102. More particularly, the first end 106a is positioned immediately upstream of the angled section 104 defined in the first needle portion 102 via a tube bending process. When properly positioned, the first end 106a may be coupled to an inner surface of the first needle portion 102 such as initially with glue and then using a manufacturing process described below.

Describing the manufacturing processes introduced above, the angled section 104 (also referred to as a bend portion 104) of the first needle portion 102 adjacent its distal end 102b is bent to a desired angle using a tube bending process. There are several methods for bending tubes, pipes, and other tubular structures, including methods (and associated dies and machines) known as press bending, rotary draw bending, three-roll push bending, induction bending, sand packing, and others. Various techniques are appropriate depending on the type of metal and other material that is being bent. Most tubular materials may be angled or bent according to a predetermined desired angle. In addition, a first end 106a of the second needle portion 106 may be securely attached to an inner surface of the tubular first needle portion 102 via a process known as crimping. In general, crimping is a process that pinches, squeezes, or otherwise tightens a friction fit connection such that the connection becomes more robust and protects against failure. For example, crimping may be used to tighten the connection of a plastic tube to a metal fitting having its slightly smaller diameter. In the present instance, crimping may be utilized to pinch together and tighten the bonds between the first needle portion 102 and the first end 106*a* of the second needle portion 106. Therefore, it is a critical aspect of the present invention that the first end 106*a* be positioned immediately upstream and adjacent to the bend portion 104 and crimped to the inner surface of the first needle portion 102 at that exact location (Although in some embodiments the first end 106*a* may be positioned even further upstream in the first needle portion 102 for even more strength and stability). Pre-bending and proper length are essential for uniform performance for injection process, more efficient delivery, staff safety, and it avoids possibility of needle stick to staff and surgeon. The construction described above is also important for patient safety as the injection needle is less likely to poke a patient in eye or deliver injection to unsafe area such as nerves or blood vessels. Again, It is critical that the first needle portion 102 be rigid as flexure or movement thereof when the surgeon is focused on the second needle portion proximate critical bodily tissues can result in unexpected and unwanted movement which may cause patient harm.

In summary, various example embodiments of the present general inventive concept may provide an injection needle including a first needle portion having a first outer diameter, and a second needle portion having a second outer diameter, the second outer diameter being smaller than the first outer diameter, wherein the second needle portion has a tip configured to penetrate a soft tissue. The injection needle 100 may include a hub 108 mounted to the first needle portion; the hub 108 being configured to mate with other similar hubs. The second needle portion 106 may form an angle with the first needle portion 102. In some example embodiments, the angle section 104 may define an angle of approximately 37 degrees. In some example embodiments, the angle may be approximately 90 degrees. The injection needle may further include a safety stop 214 positioned at an opposite end of the second needle portion from the tip, the safety stop 214 having a larger outer diameter than both the first needle portion and the second needle portion.

It is understood that while certain forms of this invention have been illustrated and described, it is not limited thereto except insofar as such limitations are included in the following claims and allowable functional equivalents thereof.

The invention claimed is:

1. An injection needle, comprising:
a first needle portion having proximal and distal ends and having a tubular configuration that defines a first outer diameter;
a second needle portion having first and second ends and having a tubular configuration that defines a second outer diameter that is smaller than the first outer diameter, said first end being positioned intermediate said proximal and distal ends of said first needle portion, said second needle portion having a tip coupled to said second end and configured to penetrate a soft tissue of a patient;
wherein said first needle portion forms an angled section at a point intermediate the proximal and distal ends thereof;
wherein said first needle portion includes a linear configuration upstream of said angled section and second needle portion includes a linear configuration downstream of said angled section;
wherein said first end of said second needle portion is positioned upstream of said angled section of said first needle portion.

2. The injection needle as in claim 1, further comprising a hub mounted to the first needle portion, the hub being configured to mate with a syringe and to deliver a pharmaceutical from said syringe to said first needle portion.

3. The injection needle as in claim 1, wherein said first end of said second needle portion is adjacent to said angled section of said first needle section.

4. The injection needle as in claim 1, wherein said first needle portion is constructed using one of metal or hard plastic.

5. The injection needle as in claim 1, wherein said angled section forms an angle of approximately 37°.

6. The injection needle as in claim 1, wherein said angled section forms an angle of approximately 45°.

7. The injection needle as in claim 1, wherein said angled section forms an angle of approximately 90°.

8. The injection needle as in claim 1, wherein said tip includes a safety stop having a larger outer diameter than both the first needle portion and the second needle portion.

9. The injection needle as in claim 1, wherein said tip includes a hypodermic needle.

10. The injection needle as in claim 1, wherein said second needle portion is crimped to said first needle portion.

11. An injection needle for use on a patient, comprising:
a hub configured to mate with a corresponding hub portion of a medication delivery device;
a first needle portion having a proximal end in fluid communication with said hub and a distal end opposite said proximal end, said first needle portion having a tubular configuration that defines a first outer diameter extending in a longitudinal direction away from the hub;
said first needle portion having a bend section intermediate said proximal and distal ends, the bend section having a predetermined angle configured to match a corresponding tissue path through which the first needle portion will pass to enter a targeted region of the patient;
a second needle portion having first and second ends and having a tubular configuration that defines a second outer diameter that is smaller than the first outer diameter, said first end being positioned intermediate said proximal and distal ends of said first needle portion,
wherein said first needle portion has a linear configuration upstream of said bend portion and said second needle portion has a linear configuration downstream of said bend portion;
wherein said first end of said second needle portion is positioned upstream of said bend section of said first needle portion;
said second end of said second needle portion terminating at a tip configured to penetrate a soft tissue of the patient.

12. The injection needle as in claim 11, wherein said first end of said second needle portion is adjacent to said bend section of said first needle section.

13. The injection needle as in claim 11, wherein said first needle portion is constructed using one of metal or hard plastic.

14. The injection needle as in claim 11, wherein said bend section forms an angle of approximately 37°.

15. The injection needle as in claim 1, wherein said bend section forms an angle of approximately 45°.

16. The injection needle as in claim 11, wherein said bend section forms an angle of approximately 90°.

17. The injection needle as in claim 11, wherein said tip includes a safety stop having a larger outer diameter than both the first needle portion and the second portion.

\* \* \* \* \*